(12) United States Patent
Van Egeraat

(10) Patent No.: US 6,487,270 B1
(45) Date of Patent: *Nov. 26, 2002

(54) APPARATUS FOR X-RAY ANALYSIS WITH A SIMPLIFIED DETECTOR MOTION

(75) Inventor: Walterus A. L. A. Van Egeraat, Almelo (NL)

(73) Assignee: Koninklijke Philips Electronics N.V., Eindhoven (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/637,250

(22) Filed: Apr. 24, 1996

(30) Foreign Application Priority Data

May 4, 1996 (EP) .............................. 95201156

(51) Int. Cl.⁷ .................................. G01T 1/36
(52) U.S. Cl. ........................................... 378/82
(58) Field of Search ......................... 378/82, 83

(56) References Cited

U.S. PATENT DOCUMENTS 3,123,710 A * 3/1964 Neuhaus ...................... 378/82
3,445,653 A * 5/1969 Tomura ........................ 378/82
5,438,613 A * 8/1995 Gijzen et al. ................ 378/83

* cited by examiner

Primary Examiner—Craig E. Church

(57) ABSTRACT

An apparatus for X-ray analysis by means of a focusing optical system according to the Rowland geometry. The apparatus is arranged to operate with a fixed measuring channel, the X-ray detector (14, 16) occupying a fixed position. In order to compensate for mechanical tolerances and a spread in the period of the analysis crystal (12) (a multilayer mirror), it is necessary to rotate the crystal slightly, after which the X-ray beam to be analyzed is no longer completely incident on the detector (14, 16). In accordance with the invention, the analysis crystal (12) is readjusted by coupling the rotation of the crystal to a displacement of the crystal in conformity with the Rowland geometry. The detector need not be displaced for as long as the angle of incidence of the X-rays to be analyzed on the analysis crystal remains small, for example <30°. It is also possible to select another wavelength to be examined, it then being merely necessarily to displace the detector along a straight line passing through the entrance slit. A guide for such a rectilinear displacement can be more readily realized than a mechanism for following the exact detector path for the Rowland geometry.

15 Claims, 2 Drawing Sheets

APPARATUS FOR X-RAY ANALYSIS WITH A SIMPLIFIED DETECTOR MOTION

The invention relates to an apparatus for X-ray analysis, comprising a source for X-rays to be analyzed, an analysis crystal for wavelength-analysis of the X-rays to be analyzed, and a detector for detecting the X-rays emanating from the analysis crystal, which analysis crystal is displaceable relative to the source along a first straight line which passes through the source, during said displacement the analysis crystal remaining tangent to a Rowland circle which extends through the source of X-rays to be analyzed and has a fixed dimension which is determined by the crystal geometry.

An X-ray analysis apparatus of this kind is known from U.S. Pat. No. 3,123,710. The apparatus described in the cited Patent, notably with reference to FIG. 1, therein is arranged to analyze fluorescence radiation emanating from a specimen to be examined. The fluorescence radiation is generated in the specimen by exposing the specimen to X-rays from an X-ray tube. Via a collimation slit (the entrance slit) the fluorescence radiation is directed onto the analysis crystal, after which the radiation originating from the crystal is collected by a detector with a collimation slit (the exit slit).

Because knowledge of the intensity distribution of the fluorescence radiation as a function of the wavelength is desired upon use of such an apparatus, the fluorescence radiation is wavelength-analyzed by the analysis crystal. This analysis is based on the well-known Bragg relation: $2d \cdot \sin\theta = n\lambda$, in which d is the distance between the X-ray reflecting faces in the analysis crystal, $\theta$ is the angle at which the radiation to be analyzed is incident on the analysis crystal, and $\lambda$ is the wavelength of the reflected radiation. This formula shows that the wavelength composition of the radiation to be analyzed can be determined by determining the intensity as a function of the angle of incidence and exit $\theta$. This is realized by displacing and rotating the analysis crystal and the detector in such a manner that all angles $\theta$ are traversed.

With a view to obtaining a suitable resolution and sensitivity, i.e. a suitable precision of measurement, the known apparatus is provided with a so-called focusing optical system, which in this case means that the entrance slit is imaged on the exit slit by the analysis crystal. This imaging effect is obtained by imparting a curved shape to the analysis crystal, for example by way of a spherical or circular-cylindrical surface, so that the analysis crystal has an imaging function in addition to an analyzing function. In order to ensure that the focusing condition is still satisfied, the entrance slit as well as the analysis crystal and the exit slit (i.e. the detector) must remain situated on a given circle, the so-called Rowland circle, during the traversing of all values of $\theta$. The diameter of this Rowland circle is determined by the radius of curvature of the analysis crystal, so that it is constant during the measurement. The position of the Rowland circle is variable during the measurement, although the fixed entrance slit and the analysis crystal should always be tangent to the Rowland circle. During execution of the measurement (a so-called $\theta$ scan) the analysis crystal is made to travel along a straight line, it being rotated in such a manner that it continues to be tangent to the Rowland circle. This straight line extends through the entrance slit which is considered to be the source of the X-rays to be analyzed for these measurements. (This is possible in that in principle no correlation exists in practice between the location and the direction of the X-rays at the area of the entrance slit as is also the case for a physical source). The detector should then follow a complex, leaf-shaped path which is commonly described as a lemniscate which should be very accurately followed. This requires a complex displacement mechanism which should satisfy very severe requirements in respect of precision and reproducibility.

A first problem is encountered if instead of carrying out a $\theta$ scan it is desired to observe only a single wavelength (for example, in order to determine the intensity distribution in a characteristic X-ray line). Generally speaking, in such a case no displacement mechanism is required for the detector and the analysis crystal, because the detector and the analysis crystal can in principle remain in a fixed position. This is referred to as a so-called fixed measuring channel which, evidently, can be substantially less expensive than a variable measuring channel for a $\theta$ scan.

In a spectrometer comprising a fixed measuring channel, the analysis crystal can thus in principle have a fixed position and orientation, but the problem then encountered is that often the orientation of the analysis crystal needs to be readjusted. Such readjustment must be performed because of the mechanical tolerances involved in the manufacture of the mounting frame and the holder for the crystal, and also because of thickness variations in the crystal itself, which variations would cause the reflected beam to be incident in the wrong location (i.e. not on the exit slit for the detector). Readjustment, moreover, is particularly necessary in the case of operation with X-rays of long wavelength, such as characteristic radiation of long light elements such as, for example borium having a characteristic radiation of a wavelength of 67 ÅE. In the case of such long wavelengths it is not possible to use a natural crystal for the analysis crystal, because the value d (the distance between the lattice faces in the crystal lattice) of such natural crystals is not of the required order of magnitude. In that case known so-called multilayer mirrors are used for wavelength analysis. A known drawback of multilayers consists in that even though the period of the layers of these mirrors is of the desired order of magnitude, it exhibits a large spread between the individual multilayer mirrors, for example of the order of magnitude of 4%. This means that a deviation of the same order of magnitude could also occur in the value of $\theta$, which deviation, in conformity with said Bragg relation, must be compensated by a corresponding variation of $\theta$, i.e. by rotation of the analysis crystal. Rotation of the analysis crystal, however, would rotate the direction of the emerging beam (i.e. the X-ray beam extending from the analysis crystal in the direction of the detector) through twice the correction angle, so that the (focused) beam would no longer reach the exit slit. If it were attempted to solve this problem by widening the exit slit, radiation would then be incident outside the actual detector material and/or too much background radiation would be collected by the detector, so that the measuring accuracy of the intensity measurements would be degraded inter alia because of a degraded signal-to-noise ratio and resolution.

It is an object of the invention to provide a solution to the problem of readjustment of the analysis crystal.

In conformity with a first aspect of the invention this problem is solved in that the apparatus comprises a fixed measuring channel in which the detector occupies a fixed position relative to the source during the measurement.

Because it is elected to move the crystal according to the known Rowland geometry during the readjustment (a motion which can be comparatively simply realized), which means that the crystal also performs a translatory motion during rotation, this motion will suffice if the angle $\theta$ is not too large. In conformity with the theory of the focusing X-ray optics the detector should follow a piece of the path of the complicated lemniscate shape during readjustment, but the invention is based on the idea that this path can be approximated by a straight line for as long as the angles θ are not too large. Thus, if the detector is made to stand still on this line-shaped part, said motion of the analysis crystal will cause only a displacement of the focus of the X-ray beam perpendicularly to the exit slit, but not noticeably in the transverse direction. Consequently, outside the focus only slight limited widening of the beam will occur; such widening is small in comparison with the total beam cross-section, because the imaging faults of the analysis crystal have already imparted a width to the beam which cannot be ignored.

Another problem occurs when a fixed measuring channel is desired for each of a number of different chemical elements (so different discrete wavelengths). In that case the comparatively complex displacement of the detector would again be necessary.

It is an object of the invention to provide a solution to this problem by providing a comparatively simple apparatus which comprises one fixed measuring channel which can be adjusted for various wavelengths.

In an apparatus of this kind the detector is displaceable with respect to the source; in conformity with a second aspect of the invention the apparatus comprises guide means for guiding the displacement of the detector along a second straight line.

Like the first aspect of the invention, the second aspect of the invention is based on the idea that this path can be approximated by a straight line, provided that the angles θ are not too large. Because the implementation of a play-free and exact straight guide motion is easier (and hence less expensive) than a prescribed curved guide motion, a much simpler apparatus is obtained.

An embodiment of the apparatus in accordance with the invention is characterized in that the analysis crystal is formed by a multilayer mirror. The spread in respect of the layer thicknesses of such a mirror in such an apparatus does not seriously affect the performance of the apparatus, mainly because it is arranged to compensate deviations in this respect.

A further embodiment of the apparatus in accordance with the invention is characterized in that the angle enclosed by the source, the analysis crystal and the detector is larger than 120°. In this case the value of θ is less than 30° (i.e. ½(180–120°)) and practice and calculations have demonstrated that the rectilinear approximation of the lemniscate path does not cause inadmissible deviations in this range.

Another embodiment yet of the apparatus in accordance with the invention is characterized in that the apparatus comprises a guide for moving therealong a point of the analysis crystal during displacement of the analysis crystal, which guide extends along a straight line passing through the source. This embodiment offers an inexpensive, play-free and accurate construction for guiding the analysis crystal along a path in conformity with the Rowland geometry.

Another embodiment of the apparatus in accordance with the invention is characterized in that the analysis crystal can be exchanged. Generally speaking, when another wavelength range of the apparatus is to be selected, a new analysis crystal will be required. When the analysis crystal is moved by means of a guide, during the manufacture of the carrier for the crystal only a different position of, for example, a guide cam cooperating with the guide need then be selected at the same setting of the relevant machine (for example, a numerically controlled milling machine). This cam can then be accurately positioned in a simple way. Even though transverse displacement of the detector will then usually be required so as to position it in the new range, the motion of the detector during the measurement will not be more complex. The transverse displacement can also be realized by inserting, for example a fixed spacer between the guide and the frame of the apparatus.

These and other aspects of the invention will be apparent from and elucidated with reference to the embodiments described hereinafter.

Figure 1:
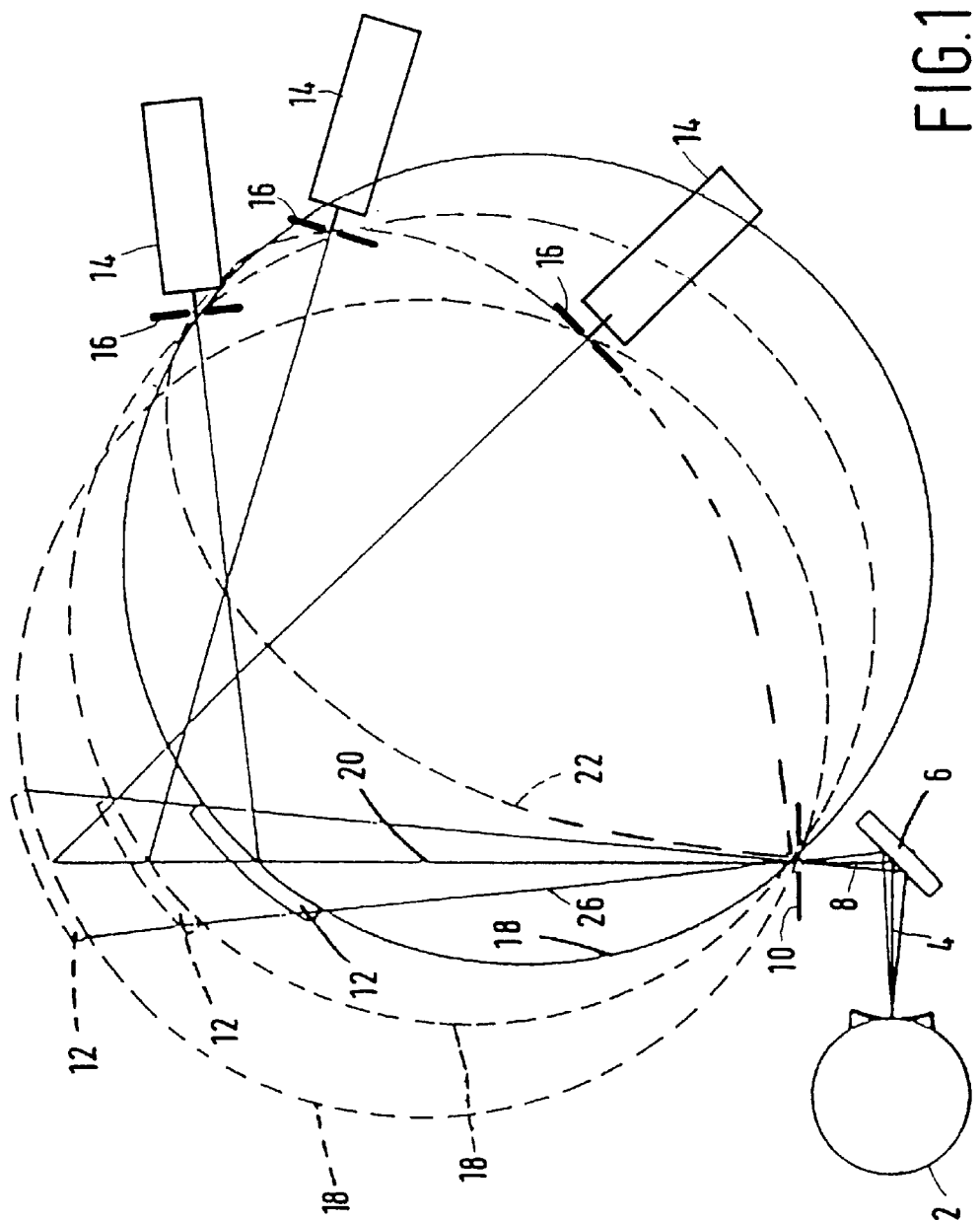
FIG. 1 is a diagrammatic representation of the motion to be performed by an analysis crystal and a detector in an X-ray analysis apparatus with a Rowland geometry.

FIG. 1 shows diagrammatically an apparatus for X-ray analysis, comprising an X-ray source 2 for generating a beam of primary X-rays 4 whereby a specimen 6 to be examined is irradiated. In the specimen 6 fluorescence radiation is generated by interaction of the primary X-rays with the material of the specimen, which fluorescence radiation provides information as regards the composition and/or the structure of the specimen. The fluorescence radiation 8 supplied by the specimen 6 is spatially bounded by means of a collimator slit 10. Because the collimator slit is situated at the entrance of the analysis apparatus, viewed from the X-ray beam, this slit is also referred to as the entrance slit. Even though from a physical point of view the X-rays are generated in the X-ray tube 2 and/or in the specimen, for evaluation of the optical properties of the analysis apparatus it is more convenient to consider the collimator slit 10 as the source of the X-rays to be analyzed.

The beam 8 of fluorescence radiation is incident on an analysis crystal 12. This crystal may be a natural crystal or an artificially formed reflective element, for example a known multilayer mirror for X-rays. For the following description it will be assumed that the analysis crystal 12 is a multilayer mirror. An analysis crystal in a spectrometer comprising a fixed measuring channel serves to select a wavelength to be measured from the beam 8 of fluorescence radiation.

The radiation emanating from the analysis crystal is captured by a detector 14, via a collimator slit 16. Because, viewed from the X-ray beam, the collimator slit 16 is situated at the exit of the analysis apparatus, this slit is also referred to as the exit slit. The exit slit 16 serves to block X-rays which do not originate from the specimen to be examined via the analysis crystal, i.e. the background radiation. The less background radiation is incident on the detector, the better the signal-to-noise ratio will be during the measurements, and hence the higher the sensitivity and the precision of the analysis apparatus will be.

For accuracy of the measurements it is advantageous when the detector of the spectrometer collects X-rays as much as possible from the collimator slit. To this end, the analysis crystal 12 has a curved surface so as to form a focusing spectrometer. It is thus achieved that the entrance slit 10 is imaged on the exit slit 16 by the curved analysis crystal 12, so that in principle all X-rays emanating from the entrance slit 10 reach the detector. Because of absorption in the path between these two slits, however, some radiation may still be lost, notably in the case of long-wave radiation such as characteristic radiation of light elements. If desired, the space in which the X-rays travel can be evacuated or filled with helium so as to counteract such absorption.

The shape of the analysis crystal may be spherical or circular cylindrical, depending on whether focusing is desired in two directions or in one direction. Its shape may also be an approximation of one of said shapes, for example a part of a logarithmic spiral which is tangent to the desired circular shape; such a spiral offers the additional advantage that said Bragg relation is satisfied over a large part of the length, so that a large part of the crystal surface can participate in the desired wavelength analysis. In order to satisfy the focusing condition throughout the measurement, the entrance slit 10, the analysis crystal 12 and the exit slit 16 should always remain on a circle 18 of fixed radius, the so-called Rowland circle. The radius of the Rowland circle is determined by the curvature of the analysis crystal, so that it has a fixed value during the measurement. In order to vary the angle of incidence of the X-rays (and hence the wavelength to be detected) during the measurement, the analysis crystal 12 is made to travel along a straight line through the entrance slit 10, the direction of the crystal being continuously readjusted in order to remain tangent to the Rowland circle. A mechanism for fixing this direction of the analysis crystal in all positions will be described with reference to FIG. 3.

FIG. 1 shows a number of positions of the analysis crystal 12, the detector 14 and the Rowland circle 18. The path 22 to be travelled by the detector during the measurement so as to remain on the Rowland circle is also shown. This path is shaped as a lemniscate. It is to be noted that the starting segment (i.e. the segment in the vicinity of the entrance slit 10) of this lemniscate 22 can be approximated by a straight line; the present invention utilizes this property.

Figure 2:
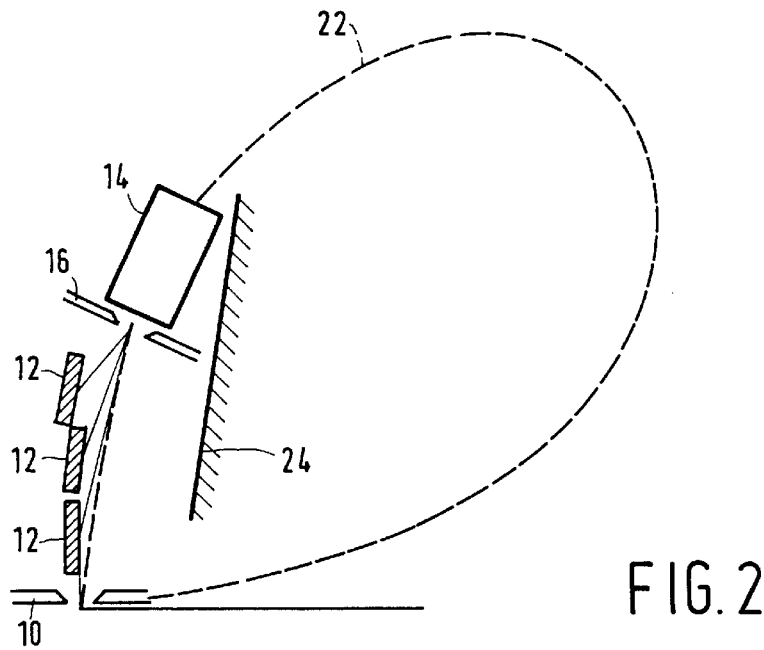
FIG. 2 is a diagrammatic representation of a part of the motion of FIG. 1.

FIG. 2 shows the lemniscate 22 and the analysis crystal in a number of positions with small angles of incidence for the X-rays to be analyzed. In this situation the analysis crystal can be subjected to displacements and rotations so that the known Rowland geometry is maintained. When the spectrometer is used as an apparatus with a fixed measuring channel, the analysis crystal 12 and the detector 14 may in principle retain a fixed position. However, a problem is then encountered in that the position of the analysis crystal must be readjusted so as to compensate for mechanical tolerances and deviations of the period of the multilayer mirror from the nominal value. The invention is based on the insight that such readjustment can take place by displacing the crystal in the range of the small angles of incidence in conformity with the Rowland geometry. The detector can then remain in its position, so that no complex mechanism will be required so as to make the detector follow the complex lemniscate path coupled to the mirror displacement. This possibility exists because for small angles of incidence the lemniscate path can be approximated by a straight line. As a result, the focus of the X-rays (actually the image of the entrance slit 10) formed by the analysis crystal describes a substantially straight path during the displacement of the analysis crystal. The exit slit 16 can then be situated, together with the detector 14, in such a manner that said line along which the focus is displaced extends perpendicularly to the plane of the exit slit 16 and passes through this slit. In the case of a moving (in the range of small angles of incidence) analysis crystal and a stationary detector, on the exit slit 16 a beam will be incident which is only slightly wider than the minimum beam width (at the area of the focus). If the exit slit is made slightly wider than said minimum width, all X-rays will be captured by the detector without the signal-to-noise ratio being significantly degraded.

In conformity with the basic idea of the invention, the measuring range of the fixed measuring signal can also be shifted, for example in order to carry out measurements on a different spectral line or to measure the background radiation. In that case it may be useful to move the detector to a different position; however, the latter position can be reached by moving the detector forwards or backwards along a straight line. Such a rectilinear displacement can be comparatively simply realized by means of a guide 24 extending parallel to said straight line.

Figure 3:
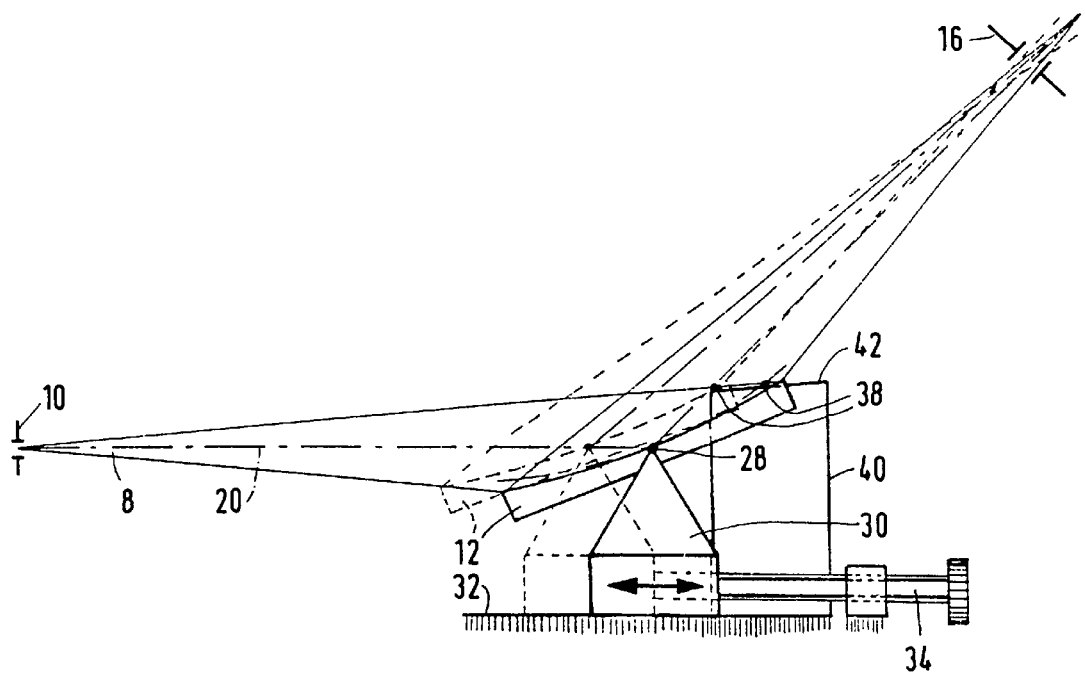
FIG. 3 shows an embodiment of a movement mechanism for the analysis crystal in accordance with the invention.

FIG. 3 shows an embodiment of a displacement mechanism for the analysis crystal in accordance with the invention. The analysis crystal 12 is shown in two positions, one of which is denoted by dashed lines, like the beam emanating from the analysis crystal. The crystal is arranged on a carrier 30 so as to be rotatable about an axis 28. The carrier is displaceable along a straight line on a guide 32. The guide extends parallel to the line 20 (see also FIG. 1), so that the pivot of the analysis crystal moves along the desired straight line 20 passing through the entrance slit 10. This rectilinear displacement is driven by an adjusting screw 34. In order to achieve the desired rotation of the analysis crystal, the crystal is provided with a cam 38 which bears on a guide 42. This guide extends parallel to (or is even coincident with) the line 26 in FIG. 1. The guide 42 forms part of a base 40 which is permanently connected to the frame of the apparatus. A shape which slightly deviates from that of a straight line can be readily imparted to the guide, so that imaging errors caused by rotation of the analysis crystal, if any, can thus be compensated for.

For adjustment of the analysis crystal 12 the adjusting screw 34 is turned, so that the carrier 30 is rectilinearly displaced. The cam 38 then travels on the guide 42, so that the correct position of the analysis crystal always remains ensured. It is thus achieved that when the analysis crystal is readjusted, the movement of the crystal always remains in conformity with the Rowland geometry. It is also feasible to drive the adjusting screw 34 by means of a motor; the intensity distribution in an X-ray peak can then be readily measured.

What is claimed is:

1. An apparatus for X-ray analysis, comprising a source for X-rays to be analyzed, an analysis crystal for wavelength-analysis of the X-rays to be analyzed, and a detector for detecting the X-rays emanating from the analysis crystal, which analysis crystal is displaceably mounted relative to the source along a first straight line which passes through the source, during displacement the analysis crystal remains tangent to a Rowland circle which has a fixed dimension which is determined by the crystal geometry, wherein said detector is displaceably mounted relative to the source, and the apparatus comprises guide means for guiding, between successive measurements, the displacement of the detector relative to the source along a second straight line which extends through the source, which straight line has a fixed position relative to the apparatus during guiding.

2. An apparatus for X-ray analysis, comprising a source (10) for X-rays (8) to be analyzed, an analysis crystal for wavelength analysis of the X-rays to be analyzed, and a detector for detecting the X-rays emanating from the analysis crystal, which analysis crystal is displaceably mounted relative to the source along a first straight line which passes through the source, so that during displacement the analysis crystal remains tangent to a Rowland circle which extends through the source of X-rays to be analyzed and has a fixed dimension which is determined by the crystal geometry, characterized in that the apparatus comprises a fixed measuring channel for allowing the detector to occupy a fixed position relative to the source during the measurement, and the apparatus lacks any mechanism for lemniscate motion.

3. An apparatus as claimed in claim 1, characterized in that the analysis crystal is formed by a multilayer mirror.

4. An apparatus as claimed in claim 1, characterized in that the angle enclosed by the source, the analysis crystal and the detector is larger than 120°.

5. An apparatus as claimed in claim 1, characterized in that the apparatus comprises a guide for moving therealong a point of the analysis crystal during displacement of the analysis crystal, which guide extends along a straight line passing through the source.

6. An apparatus as claimed in claim 5, characterized in that the analysis crystal can be exchanged.

7. X-ray analysis apparatus for conducting a small θ scan or an adjustment between single wavelength measurements, the apparatus comprising:

a. a source for x-rays to be analyzed;

b. an analysis crystal for wavelength analysis of the x-rays to be analyzed;

c. a detector for detecting the x-rays emanating from the analysis crystal; and d. a crystal adjuster for first displacing the analysis crystal along a first straight line that passes through the source, the analysis crystal remaining tangent to a Rowland circle during the first displacement, the Rowland circle extending through the source of x-rays to be analyzed and having a fixed dimension that is determined by the crystal geometry; and e. a detector adjuster for second displacing the detector along a second straight line that passes through the source, which second straight line does not move during any measurement or adjustment, any such first and/or second displacement effectuating the scan or adjustment; whereby no mechanism for lemniscate motion is required for the scan or adjustment.

8. An apparatus as claimed in claim 7, characterized in that the analysis crystal is formed by a multilayer mirror.

9. An apparatus as claimed in claim 7, characterized in that the angle enclosed by the source, the analysis crystal and the detector is larger than 120°.

10. An apparatus as claimed in claim 7, characterized in that the analysis crystal can be exchanged.

11. X-ray analysis apparatus for conducting a small θ scan or an adjustment between single wavelength measurements, the apparatus comprising:

a. a source for x-rays to be analyzed;

b. an analysis crystal for wavelength analysis of the x-rays to be analyzed;

c. a detector for detecting the x-rays emanating from the analysis crystal, the detector and source being mounted so that the detector occupies a fixed position relative to the source during the scan or adjustment; and d. a crystal adjuster for displacing the analysis crystal along a straight line that passes through the source, the analysis crystal remaining tangent to a Rowland circle during the displacement, the Roland circle extending through the source and having a fixed dimension which is determined by the crystal geometry, the displacement effectuating the scan or adjustment;

whereby no mechanism for lemniscate motion is required for the scan or adjustment.

12. The apparatus of claim 7, wherein the adjuster further comprises a carrier for carrying the analysis crystal along the guide means, the carrier including an axis upon which the analysis crystal is rotatably disposed.

13. The apparatus of claim 11 wherein the analysis crystal comprises multi-layered mirror means and the adjustment compensates for a spread between an expected and an actual period of the mirror means.

14. The apparatus of claim 11 wherein the adjuster comprises a carrier for removably mounting the analysis crystal and the adjustment compensates for a change of analysis crystal.

15. The apparatus of claim 14 wherein the measurement is a fixed wavelength measurement and the adjustment compensates for a substitution of a second crystal for a first crystal, the first crystal allowing the measurement at a first, fixed wavelength and the second crystal allowing measurement at a second, fixed wavelength, which second wavelength is distinct from the first wavelength.

\* \* \* \* \*